United States Patent [19] [11] Patent Number: 4,670,390
Antal née Magyar et al. [45] Date of Patent: Jun. 2, 1987

[54] PROCESS FOR THE IMMOBILIZATION OF COMPOUNDS COMPRISING NUCLEOPHILIC GROUPS

[75] Inventors: Zsuzsanna Antal née Magyar, Budapest; Éva Bellér, Szeged; László Boross; Iván Daróczi, both of Budapest; Miklós Kálmán, Szeged; Imre Sütő; Béla Szajáni, both of Budapest, all of Hungary

[73] Assignee: Reanal Finomvegyszergyar, Budapest, Hungary

[21] Appl. No.: 526,035

[22] Filed: Aug. 24, 1983

[30] Foreign Application Priority Data

Aug. 24, 1982 [HU] Hungary .............................. 2719/82

[51] Int. Cl.$^4$ ...................... C12N 11/08; C12N 11/02; C12N 11/06; C12N 11/00
[52] U.S. Cl. .................................... 435/180; 435/174; 435/177; 435/181; 436/532; 525/54.1; 525/54.2; 525/384
[58] Field of Search ............... 435/174, 177, 180, 181; 525/54.1, 54.2, 384; 436/532

[56] References Cited

U.S. PATENT DOCUMENTS 3,836,433 9/1974 Wirth et al. ........................ 435/181
4,193,982 3/1980 Avrameas et al. .................. 436/512
4,282,343 8/1981 Platt, Jr. ............................. 525/336

OTHER PUBLICATIONS

Morrison R. and R. Boyd, *Organic Chemistry*, 3rd Edition, Allyn and Bacon, Inc. Boston, 1973, (p. 617).
Brandt et al. "Covalent Attachment of Proteins to Polysaccharide Carriers by Means of Benzoquinone," *Biochimica et Biophysica Acta*, vol. 386, 1975, pp. 192-202.
Avrameas et al. *Scand. J. Immunol.* (Engvall et al., eds.), Suppl. 7, vol. 8, Blackwell Scientific Publications, Oxford, pp. 12 and 21, (1978).
Morrison et al. *Archives of Biochem. and Biophysics*, 134, pp. 515-523 (1969).
*Hackh's Chemical Dictionary*, Grant, 4th Edition, p. 400, McGraw-Hill, 1968.
Goldstein et al., *The Chemistry of Enzyme Immobilization*, pp. 23-77, Academic Press, New York.
*Organic Chemistry, A Short Course*, Sixth Edition, Harold Hart, pp. 290-304.
Fodor: "Szerves Kemia" (Organic Chemistry) pp. 899-902.
*Organic Chemistry: An Overview*, Moore et al, pp. 236-241.
*Fundamentals of Organic Chemistry*, Bonner and Castro, p. 105, (1966).

Primary Examiner—Sidney Marantz
Assistant Examiner—Patricia Kate White
Attorney, Agent, or Firm—Karl F. Ross; Herbert Dubno

[57] ABSTRACT

The invention relates to a process for the immobilization of compounds comprising nucleophilic groups.

According to the process of the invention a polymer comprising an amido group is swollen in a buffer. For this purpose any buffer is suitable which contains no amino, sulfhydryl and/or hydroxy groups in the molecule. To the swollen polymer a solution of a quinone - preferably p-benzoquinone - in a water miscible organic solvent is added and the mixture is activated at 273°-343° K. for 0.5-48 hours - preferably for 24 hours. The unreacted quinone is washed out with an aqueous solution of a water miscible organic solvent and thereafter water and/or a buffer. To the purified gel at a pH value between 3 and 11 - preferably between 6 and 8 - a buffered solution of a compound comprising a nucleophilic group is added, the suspension is incubated at 260°-313° K. for 24 hours, the gel is separated and the non-bound compound comprising a nucleophilic group is removed by washing.

8 Claims, No Drawings

PROCESS FOR THE IMMOBILIZATION OF COMPOUNDS COMPRISING NUCLEOPHILIC GROUPS

This invention relates to a process for the immobilization of compounds comprising nucleophilic groups. More particularly it is concerned with a process for the immobilization of compounds comprising nucleophilic groups (e.g. amino acids, peptides, proteins, carbohydrates etc.) by means of polymers which contain carboxylic acid amide groups activated by a quinone.

In the last years several procedures were elaborated for the immobilization of compounds having lower molecular weight or biopolymers (e.g. proteins) on a solid phase carrier [Zaborsky, O. R. (1973) "Immobilized Enzymes" (West, R. C., ed.), CRC Press, Cleveland, Ohio; Chibata, I. (1978) "Immobilized Enzymes" (Chibata, I., ed.), pp. 9-107, Kodansha, Ltd., Tokyo; Goldstein, L., Manecke, G. (1979) "Applied Biochemistry and Bioengineering" (Wingard, L. B., Katchalski-Katzir, E. and Goldstein, L., eds.), Vol. 1, pp. 23-126, Academic Press. Inc., New York].

The general drawbacks of the above known methods can be summarized as follows:
special reaction conditions are required;
by some methods the bond between the carrier and the ligand is formed with the aid of special coupling agents;
some of the coupling agents are highly toxic compounds (e.g. thiophosgene) and therefore special and expensive safety measures must be effectuated.

The object of the present invention is to overcome the disadvantages of the known methods and to provide a process for the immobilization of compounds comprising nucleophilic groups through covalent bonds, the said process being readily feasible under simple conditions with the aid of significantly less toxic activating agents and on easily available, advantageous carriers which can be manufactured on an industrial scale.

The present invention is based on the surprising recognition that the polymers comprising amido groups enter into interaction with quinones and the activated polymers thus formed are capable of binding compounds which comprise a nucleophilic group by covalent bonds. The above recognition is even more unaforeseen as it is known that carboxylic acid amides are rather less reactive compounds and on the basis of the state of the prior art the skilled art worker could not expect that the compounds would react with quinones.

According to the process of the present invention the immobilization of compounds comprising a nucleophilic group is carried out in two stages:

(1) The polymer comprising the amido group is swollen in a buffer having a pH value of 3-11, preferably 6-8. Any polymer can be used in the process of the present invention. Any buffer is suitable for the purposes of the present invention as well, with the provision that it should not contain compounds comprising an amino, sulfhydryl and/or hydroxy group. The solution of the quinone formed with any suitable water-miscible organic solvent is then added. As quinone preferably p-benzoquinone and as organic solvent preferably ethanol or dioxane may be used. In the solution the final concentration of the p-benzoquinone amounts to 2-100 millimoles, preferably 40-60 millimoles. The activation is carried out at 273°-343° K. and the reaction time is 0.5-48 hours—preferably 24 hours. The unreacted excess of p-benzoquinone is removed by washing with a mixture of water and a water-miscible organic solvent—preferably 20% dioxanel—and thereafter with a buffer. The activated carrier can be stored in wet form or in a lyophilized state.

(2) The immobilization of the compounds comprising a nucleophilic group is carried out at a pH interval of 3-11, preferably between 6 and 8, depending on the stability of the compound. To the activated gel a solution of the compound comprising a nucleophilic group is added. Compounds of low molecular weight are added in the form of a 0.001-1.0 molar—preferably 0.01 molar solution, while the concentration of the solution of the macromolecular compounds amounts to 3-100 mg/ml, preferably 20 mg/ml. The coupling reaction is carried out at 260°-313° K., preferably at 273°-280° K. The reaction time amounts to 24 hours.

The non-bound compound comprising a nucleophilic group is removed by washing several times with a buffer and a buffer comprising 1.0 mole of sodium chloride, respectively.

The advantages of the process of the present invention are the following:
a stable bond is formed;
the process can be carried out by using readily available substances;
the process works on a wide range of carriers;
the process is applicable in a wide pH range.

Further details of the present invention are found in the Examples without limiting the scope of the invention to the said Examples.

EXAMPLE 1

30 g of Akrilex P-100 xerogel (acrylamide-N,N'-methylene-bis-acrylamide copolymer) are suspended in 1200 ml of a 0.1 molar potassium sodium phosphate buffer (pH=8), whereupon a solution of 0.25 mole of p-benzoquinone in 20% dioxane (300 ml) is added and the suspension is allowed to stand at 323° K. for 24 hours. The swollen gel is removed and washed subsequently with 3 l of 20% dioxane and 10 l of distilled water. The washed gel is subjected to lyophilization. Thus 24.3 g of an activated carrier are obtained.

EXAMPLE 2

0.1 g of Akrilex P-100 xerogel (acrylamide-N,N'-methylene-bis-acrylamide copolymer) is suspended in 4.0 ml of a 0.1 molar phosphate buffer (pH 8.0), whereupon a solution of 0.25 mole of p-benzoquinone in 20% dioxane (1.0 ml) is added and the suspension is allowed to stand at 323° K. for 24 hours. The swollen gel is separated and washed subsequently with 70 ml of 20% dioxane and 70 ml of distilled water.

The activated gel is filtered in vacuo and 2.0 ml of a 0.01 molar γ-amino-butyric acid solution are added. For the solubilization of the γ-amino-butyric acid a 0.1 molar potassium sodium phosphate buffer is used (pH 7.5). The suspension is incubated at 277° K. for 24 hours, the gel is separated and the non-bound γ-amino-butyric acid is removed by washing with a 0.1 molar sodium acetate buffer comprising 1.0 mole of sodium chloride (5.0) and a 0.1 molar sodium hydrogen carbonate solution (pH 8.5). Thus 4 micromoles of γ-amino-butyric acid are bound which corresponds to to 20% of the amount of γ-amino-butyric acid added to the reaction mixture.

EXAMPLE 3

0.1 g of Akrilex P-100 xerogel (acrylamide-N,N'methylene-bis-acrylamide copolymer) is suspended in 4.0 ml of a 0.1 molar phosphate buffer (pH 8.0), whereupon a solution of 0.25 mole of p-benzoquinone in 20% dioxane (1.0 ml) is added and the suspension is allowed to stand at 323° K. for 24 hours. The swollen gel is separated and washed subsequently with 70 ml of 20% dioxane and 70 ml of distilled water.

The activated gel is filtered in vacuo, whereupon 2.0 ml of a 20 mg/ml bovine serum albumin solution is added. In order to enhance the dissolution of the bovine serum albumin a 0.1 molar sodium formiate buffer (pH 3.0) is used. The suspension is incubated for 24 hours at 277° K. the gel is separated and the non-bound serum albumin is removed by washing with a 0.1 molar sodium acetate buffer comprising 1.0 mole of sodium chloride (pH 5.0) and a 0.1 molar sodium hydrogen carbonate solution (pH 8.5). Thus 10 mg of serum albumin are bound which corresponds to 25% of the amount of the serum albumin added to the reaction mixture.

EXAMPLE 4

0.1 g of Akrilex P-100 xerogel (acrylamide-N,N'methylene-bis-acrylamide copolymer) is suspended in 4.0 ml of a 0.1 molar phosphate buffer (pH 8.0), whereupon a solution of 0.25 mole of p-benzoquinone in 20% dioxane (1.0 ml) is added and the suspension is allowed to stand at 323° K. for 24 hours. The swollen gel is separated and washed subsequently with 70 ml of 20% dioxane and 70 ml of distilled water.

The activated gel is filtered in vacuo, whereupon 2.0 ml of a 20 mg/ml bovine serum albumin solution is added. A 0.1 molar potassium-sodium phosphate buffer (pH 6.0) is used to facilitate the dissolving of the bovine serum albumin. The suspension is incubated at 277° K. for 24 hours, the gel is separated and the non-bound serum albumin is removed by washing with 0.1 mole a 0.1 molar sodium acetate buffer comprising 1.0 mole of sodium chloride (pH 5.0) and a 0.1 molar hydrogen carbonate solution (pH 8.5). Thus 4.5 mg of bovine serum albumin are bound which corresponds to 11.25% of the serum albumin added to the reaction mixture.

EXAMPLE 5

0.1 g of Akrilex P-100 xerogel (acrylamide-N,N'methylene-bis-acrylamide copolymer) is suspended in 4.0 ml of a 0.1 molar phosphate buffer (pH 8.0), whereupon a solution of 0.25 mole of p-benzoquinone in 20% dioxane (1.0 ml) is added and the suspension is allowed to stand at 323° K. for 24 hours. The swollen gel is separated and washed subsequently with 70 ml of 20% dioxane and 70 ml of distilled water.

The activated gel is filtered in vacuo, whereupon 2.0 ml of a 20 mg/ml bovine serum albumin solution is added. A 0.1 molar sodium carbonate-sodium hydrogen carbonate buffer (pH 9.0) is used to facilitate the dissolving of the bovine serum albumin. The suspension is incubated at 277° K. for 24 hours, the gel is separated and the non-bound serum albumin is removed by washing with a 0.1 molar sodium acetate buffer comprising 1.0 mole of sodium chloride (pH 5.0) and a 0.1 molar sodium hydrogen carbonate solution (pH 8.5). Thus 5.0 mg of bovine serum albumin are bound which corresponds to 12.5% of the serum albumin added to the reaction mixture.

EXAMPLE 6

0.1 g of Akrilex P-100 xerogel (acrylamide-N,N'methylene-bis-acrylamide copolymer) is suspended in 4.0 ml of a 0.1 molar phosphate buffer (pH 8.0), whereupon a solution of 0.25 mole of p-benzoquinone in 20% dioxane (1.0 ml) is added and the suspension is allowed to stand at 323° K. for 24 hours. The swollen gel is separated and washed subsequently with 70 ml of 20% dioxane and 70 ml of distilled water.

The activated gel is filtered in vacuo and 2.0 ml of a 20 mg/ml glucooxidase solution are added. The dissolution of the glucooxidase in promoted with the aid of a 0.1 molar potassium sodium phosphate buffer (pH 7.5). The suspension is incubated at 277° K. for 4 hours, the gel is separated and the non-bound protein is removed by washing with a 0.1 molar sodium acetate buffer comprising 1.0 mole of sodium chloride (pH 5.0) and a 0.1 molar sodium hydrogen carbonate solution (pH 8.5).

The amount of the protein bound on the gel is 4.5 mg, the activity being 7.2 units/g xerogel. 1 unit corresponds to an amount of the enzyme which is capable of catalyzing the oxidation of 1.0 micromole of $\beta$-D-glucose at 7.0° and 298° K. per minute. The specific activity of the bound enzyme amounts to 8% of that of the dissolved enzyme.

EXAMPLE 7

0.1 g of Akrilex P-100 xerogel (acrylamide-N,N'methylene-bis-acrylamide copolymer) is suspended in 4.0 ml of a 0.1 molar phosphate buffer (pH 8.0), whereupon a solution of 0.25 mole of p-benzoquinone in 20% dioxane (1.0 ml) is added and the suspension is allowed to stand at 323° K. for 24 hours. The swollen gel is separated and washed subsequently with 70 ml of 20% dioxane and 70 ml of distilled water.

The activated gel is filtered in vacuo and 2.0 ml of a 20 mg/ml catalase solution are added. The dissolution of the catalase is enhanced by using a 0.1 molar potassium sodium phosphate buffer (pH 7.5). The suspension is incubated at 277° K. for 24 hours, the gel is separated and the non-bound protein is removed by washing with a 0.1 molar sodium acetate buffer comprising 1.0 mole of sodium chloride (pH 5.0) and a 0.1 molar sodium hydrogen carbonate solution (pH 8.5).

The amount of the protein bound on the gel is 5.3 mg, the activity being 2100 units/g xerogel. 1 unit corresponds to the amount of enzyme which is capable of catalyzing the decomposition of 1 micromole of hydrogen peroxide per minute at 298° K. The specific activity of the bound enzyme amounts to 2% of that of the dissolved enzyme.

EXAMPLE 8

0.1 g of Akrilex P-100 xerogel (acrylamide-N,N'methylene-bis-acrylamide copolymer) is suspended in 4.0 ml of a 0.1 molar phosphate buffer (pH 8.0), whereupon a solution of 0.25 mole of p-benzoquinone in 20% dioxane (1.0 ml) is added and the suspension is allowed to stand at 323° K. for 24 hours. The swollen gel is separated and washed subsequently with 70 ml of 20% dioxane and 70 ml of distilled water.

The activated gel is filtered in vacuo and 2.0 ml of a 0.01 molar glucose solution are added. The dissolution of the glucose is promoted by using a 0.1 molar potassium sodium phosphate buffer (pH 7.5). The suspension is incubated at 277° K. for 24 hours, the gel is separated and the non-bound glucose is removed by washing subsequently with a 0.1 molar sodium acetate buffer comprising 1.0 mole of sodium chloride (pH 5.0) and a 0.1 molar sodium hydrogen carbonate solution (pH 8.5). Thus 6 microns of glucose are bound which corresponds to 30% of the amount of glucose added to the reaction mixture.

What we claim is:

1. A process for the immobilization of a macromolecular compound comprising a nucleophilic group which comprises the steps of:
    (a) swelling a polymer which contains an amido group in a buffer having a pH value between 3 and 11 wherein said buffer contains no amino, sulfhydryl or hydroxy group;
    (b) activating said polymer to react with said macromolecular compound by adding to said polymer a solution of a benzoquinone in an inert water-miscible organic solvent in such an amount that the final concentration of the benzoquinone is 2–100 millimole to form a covalent bond between the amido group of said polymer and said benzoquinone;
    (c) allowing the polymer treated according to step (b) with the solution of the benzoquinone in the inert water-miscible organic solvent to stand for a period of 0.5 to 48 hours at 273° to 343° K. to form a gel;
    (d) removing any non-reacted benzoquinone from the gel by washing the latter with a mixture of water and an inert water-miscible organic solvent and thereafter with distilled water, with a buffer or with both;
    (e) adding to the gel at a pH value between 3 and 11 a 3 to 100 mg/ml solution of said macromolecular compound to form a suspension;
    (f) incubating the suspension at 260° to 313° K. for 24 hours to immobilize said macromolecular compound; and
    (g) washing the suspension with a 0.1 molar sodium acetate buffer comprising 1.0 mole of sodium chloride and then with a 0.1 molar sodium bicarbonate solution to remove any unreacted macromolecular compound from said immobilized macromolecular compound prepared as a gel.

2. A process defined in claim 1 wherein said macromolecular compound comprising a nucleophilic group is a protein.

3. The process defined in claim 1 wherein said macromolecular compound comprising a nucleophilic group is selected from the group consisting of bovine serum albumin, glucooxidase, and catalase.

4. The process defined in claim 1, wherein the step (a), the polymer containing an amido group is acrylamide-N,N'-methylene-bis-acrylamide copolymer.

5. A process for the immobilization of a low molecular weight compound comprising a nucleophilic group which comprises the steps of:
    (a) swelling a polymer which contains an amido group in a buffer having a pH value between 3 and 11 wherein said buffer contains no amino, sulfhydryl, or hydroxy group;
    (b) activating said polymer to react with said low molecular weight compound by adding thereto a solution of a benzoquinone in an inert water-miscible organic solvent in such an amount that the final concentration of the benzoquinone is 2–100 millimoles to form a covalent bond between the amido group of said polymer and said benzoquinone;
    (c) allowing the polymer treated according to step (b) with the solution of a benzoquinone in the inert water-miscible-organic solvent to stand for a period of 0.5 to 48 hours at 273° to 343° K. to form a gel;
    (d) removing any non-reacted benzoquinone from the gel by washing the latter with a mixture of water and an inert water-miscible organic solvent and thereafter with distilled water, with a buffer, or with both;
    (e) adding to the gel at a pH value between 3 and 11 a 0.001 to 1.0 molar solution of said low molecular weight compound comprising a nucleophilic group to form a suspension;
    (f) incubating the suspension at 260° to 313° K. for 24 hours to immobilize said low molecular weight compound comprising a nucleophilic group; and
    (g) washing the suspension with a 0.1 molar sodium acetate buffer comprising 1.0 mole of sodium chloride and then with a 0.1 molar sodium bicarbonate solution to remove any unreacted low molecular weight compound from said immobilized low molecular weight compound prepared as a gel.

6. The process defined in claim 5 wherein said low molecular weight compound is a carbohydrate or an amino acid.

7. The process defined in claim 6 wherein said low molecular weight compound is glucose or gamma-amino-butyric acid.

8. The process defined in claim 5 wherein in step (a) the polymer containing an amido group is acrylamide-N,N'-methylene-bis-acrylamide copolymer.

* * * * *